US008507443B2

(12) United States Patent
Mekada et al.

(10) Patent No.: US 8,507,443 B2
(45) Date of Patent: Aug. 13, 2013

(54) ANTICANCER AGENT

(75) Inventors: Eisuke Mekada, Suita (JP); Shingo Miyamoto, Fukuoka (JP)

(73) Assignee: The Research Foundation for Microbial Diseases of Osaka University, Suita-shi Osaka (JP)

( * ) Notice: Subject to any disclaimer, the term of this patent is extended or adjusted under 35 U.S.C. 154(b) by 1268 days.

(21) Appl. No.: 11/885,080

(22) PCT Filed: Aug. 19, 2005

(86) PCT No.: PCT/JP2005/015135
§ 371 (c)(1),
(2), (4) Date: Dec. 17, 2007

(87) PCT Pub. No.: WO2006/090494
PCT Pub. Date: Aug. 31, 2006

(65) Prior Publication Data
US 2011/0230418 A1 Sep. 22, 2011

(30) Foreign Application Priority Data
Feb. 25, 2005 (JP) .................................. 2005-052165

(51) Int. Cl.
*A61K 38/16* (2006.01)
*A61K 31/337* (2006.01)
*C07D 471/22* (2006.01)

(52) U.S. Cl.
USPC .......... 514/19.4; 514/21.2; 514/449; 546/122

(58) Field of Classification Search
None
See application file for complete search history.

(56) References Cited

FOREIGN PATENT DOCUMENTS
JP 2004-155776 A 6/2004
WO WO 03/045429 A2 6/2003

OTHER PUBLICATIONS

McGuire et al. ("Primary ovarian cancer chemotherapy: current standards of care," British Journal of Cancer, 89 (Suppl 3), S3-S8, 2003).*
Higashiyama et al., Heparin-binding EGF-like Growth Factor Stimulation of Smooth Muscle Cell Migration: Dependence on Interactions with Cell Surface Heparin Sulfate, The Journal of Cell Biology, 122(4): 933-940 (1993).
Prenzel et al., EGF Receptor Transactivation by G-Protein-Coupled Receptors Requires Metalloproteinase Cleavage of ProHB-EGF, Nature, 402:884-888 (1999).
Naglich et al., Expression Cloning of a Diphtheria Toxin Receptor: Identity with a Heparin-Binding EGF-like Growth Factor Precursor, The Journal of Cell Biology, 69:1051-1061 (1992).
Mitamura et al., Diphtheria Toxin Binds to the Epidermal Growth Factor (EGF)-like Domain of Human Heparin-Binding EGF-like Growth Factor /Diphtheria Toxin Receptor and Inhibits Specifically Its Mitogenic Activity, The Journal of Biological Chemistry, 270(8):1015-1019 (1995).
Umata et al., Diphtheria Toxin Translocation across Endosome Membranes, The Journal of Biological Chemistry, 273(14):8351-8359 (1998).
Shen et al., Participation of Lysine 516 and Phenylalanine 530 of Diphtheria Toxin in Receptor Recognition, The Journal of Biological Chemistry, 269( 46)29077-29084 (1994).
Gordon et al., Crystal Structure of the Complex of Diphtheria Toxin with an Extracellular Fragment of Its Receptor, Molecular Cell, 1: 67-68 (1997).
Miyamoto et al., Heparin-Binding EGF-Like Growth Factor Is a Promising Target for Ovarian Cancer Therapy, Cancer Research, 64(16):5720-5727 (2004).
Younes, et al., Three-hour Paclitaxel Infusion in Patients with Refractory and Relapsed Non-Hodgkin's Lymphoma, Journal of Clinical Oncology, 13(3):583-587 (1995).
Mekada, et al., Idenshi Igaku, 5(2):p. 131-134 (2001) (with translation).
Miyamoto et al. Ransogan Hyoteki Chiryoyaku CRM197 to Taxol tono Heiyo Koka ni Kansuru Kenkyu, Acta Obstetrica et Gynaecologia Japonica, 57(2):610, p. 2-51 (2005) (with translation).
Miyamoto et al., Heparin Binding Epidermal Growth Factor Like Growth Factor (HB) ni Taisuru Rangan Bunshi Hyoteki Chiryo no Koka, The Japanese Cancer Association Sokai Kiji 63$^{rd}$, 429-430 W-433 (2004) (with translation).
Kabushiki Kaisha, "Taxol Injection", Bristol-Myers, pp. 1-5, Ninth Edition, Sep. 2004 (including partial English translation).
Decision of Final Rejection dated Mar. 15, 2011, in corresponding Japanese Application No. 2005-052165.
Silvio Buzzi; "Diphtheria Toxin Treatment of Human Advanced Cancer", Cancer Research 42, 2054-2058, (May 1982).
Silvio Buzzi, et al.; "Phase I-II study of CRM197 administration to 50 advanced cancer patients", Clinical Cancer Research, vol. 5, #384 (Nov. 1999) (Supplement).
Silvio Buzzi, et al.; "CRM197: Phagocyte mediated antitumor activity followed by a connective proliferation tending to encapsule the tumor", Proceedings of the American Association for Cancer Research, vol. 43, #4529 (Mar. 2002).
Silvio Buzzi; "Diphtheria Toxin in Cancer Therapy", The Lancet, 628-629 (Apr. 6, 1974).
Silvio Buzzi, et al.; "Diphtheria toxoid immunotherapy of human advanced cancer", Proceedings of the American Association for Cancer Research, vol. 35, #3150 (Mar. 1994).

(Continued)

*Primary Examiner* — Christina Bradley
(74) *Attorney, Agent, or Firm* — Fitch, Even, Tabin & Flannery, LLP

(57) ABSTRACT

The present invention is an antineoplastic agent characterized by including at least one of taxol and taxol derivatives and a protein which is a mutant of diphtheria toxin, having an activity to inhibit a binding between HB-EGF and EGFR and substantially not having a toxicity of diphtheria toxin as active ingredients.

10 Claims, 9 Drawing Sheets

(56) References Cited

OTHER PUBLICATIONS

Silvio Buzzi, et al.; "Immunological effects of a boiled diphtheria toxoid on high risk cancer patients", Proceedings of the American Association for Cancer Research, vol. 38, #2662 (Mar. 1997).

Silvio Buzzi, et al.; "CRM197: effects in cancer patients", Proceedings of the American Association for Cancer Research, vol. 39, #2412 (Mar. 1998).

Silvio Buzzi, et al.; "Antitumor Effect of CRM197: Preferential Activity in Lymph Nodes", Proceedings of the American Association for Cancer Research, vol. 41, #1839 (Mar. 2000).

Silvio Buzzi, et al.; "Cancer Immunotherapy with CRM197, A Nontoxic Mutant of Diphtheria Toxin", Abstracts of the Oncology—Molecular Medicine Congress, #185 (2001).

Silvio Buzzi, et al.; "CRM197 antitumor activity: Possible mechanism of action", Proceedings of the American Association for Cancer Research, vol. 44, #3857 (Mar. 2003).

Silvio Buzzi, et al.; "CRM197; Effects of intravenous administration to advanced cancer patients", American Association for Cancer Research, #3803 (2004).

Silvio Buzzi, et al.; "CRM197 (nontoxic diphtheria toxin): effects on advanced cancer patients", Cancer Immunol. Immunother 53, 1041-1048 (2004).

\* cited by examiner

FIG. 2

```
          10        20        30        40        50        60
GTGAGCAGAAAACTGTTTGCGTCAATCTTAATAGGGGCGCTACTGGGGATAGGGGCCCCA
 M  S  R  K  L  P  A  S  I  L  I  G  A  L  L  G  I  G  A  P  -6

70        80        90       100       110       120
CCTTCAGCCCATGCAGGCGCTGATGATGTTGTTGATTCTTCTAAATCTTTTGTGATGGAA
 P  S  A  H  A  G  A  D  D  V  V  D  S  S  K  S  F  V  M  E  15

130       140       150       160       170       180
AACTTTTCTTCGTACCACGGGACTAAACCTGGTTATGTAGATTCCATTCAAAAAGGTATA
 N  F  S  S  Y  H  G  T  K  P  G  Y  V  D  S  I  Q  K  G  I  35

190       200       210       220       230       240
CAAAAGCCAAAATCTGGTACACAAGGAAATTATGACGATGATTGGAAAGGGTTTTATAGT
 Q  K  P  K  S  G  T  Q  G  N  Y  D  D  D  W  K  G  F  Y  S  55

250       260       270       280       290       300
ACCGACAATAAATACGACGCTGCGGGATACTCTGTAGATAATGAAAACCCGCTCTCTGGA
 T  D  N  K  Y  D  A  A  G  Y  S  V  D  N  E  N  P  L  S  G  75

310       320       330       340       350       360
AAAGCTGGAGGCGTGGTCAAAGTGACGTATCCAGGACTGACGAAGGTTCTCGCACTAAAA
 K  A  G  G  V  V  K  V  T  Y  P  G  L  T  K  V  L  A  L  K  95

370       380       390       400       410       420
GTGGATAATGCCGAAACTATTAAGAAAGAGTTAGGTTTAAGTCTCACTGAACCGTTGATG
 V  D  N  A  E  T  I  K  K  E  L  G  L  S  L  T  E  P  L  M  115

430       440       450       460       470       480
GAGCAAGTCGGAACGGAAGAGTTTATCAAAAGGTTCGGTGATGGTGCTTCGCGTGTAGTG
 E  Q  V  G  T  E  E  F  I  K  R  F  G  D  G  A  S  R  V  V  135

490       500       510       520       530       540
CTCAGCCTTCCCTTCGCTGAGGGGAGTTCTAGCGTTGAATATATTAATAACTGGGAACAG
 L  S  L  P  F  A  E  G  S  S  S  V  E  Y  I  N  N  W  E  Q  155

550       560       570       580       590       600
GCGAAAGCGTTAAGCGTAGAACTTGAGATTAATTTTGAAACCCGTGGAAAACGTGGCCAA
 A  K  A  L  S  V  E  L  E  I  N  F  E  T  R  G  K  R  G  Q  175

610       620       630       640       650       660
GATGCGATGTATGAGTATATGGCTCAAGCCTGTGCAGGAAATCGTGTCAGGCGATCAGTA
 D  A  M  Y  E  Y  M  A  Q  A  C  A  G  N  R  V  R  R  S  V  195

670       680       690       700       710       720
GGTAGCTCATTGTCATGCATAAATCTTGATTGGGATGTCATAAGGGATAAAACTAAGACA
 G  S  S  L  S  C  I  N  L  D  W  D  V  I  R  D  K  T  K  T  215

730       740       750       760       770       780
AAGATAGAGTCTTTGAAAGAGCATGGCCCTATCAAAAATAAAATGAGCGAAAGTCCCAAT
 K  I  E  S  L  K  E  H  G  P  I  K  N  K  M  S  E  S  P  N  235

790       800       810       820       830       840
AAAACAGTATCTGAGGAAAAAGCTAAACAATACCTAGAAGAATTTCATCAAACGGCATTA
 K  T  V  S  E  E  K  A  K  Q  Y  L  E  E  F  H  Q  T  A  L  255

850       860       870       880       890       900
GAGCATCCTGAATTGTCAGAACTTAAAACCGTTACTGGGACCAATCCTGTATTCGCTGGG
 E  H  P  E  L  S  E  L  K  T  V  T  G  T  N  P  V  F  A  G  275
```

FIG. 3

```
         910       920       930       940       950       960
GCTAACTATGCGGCGTGGGCAGTAAACGTTGCGCAAGTTATCGATAGCGAAACAGCTGAT
 A  N  Y  A  A  W  A  V  N  V  A  Q  V  I  D  S  E  T  A  D  295

970       980       990      1000      1010      1020
AATTTGGAAAAGACAACTGCTGCTCTTTCGATACTTCCTGGTATCGGTAGCGTAATGGGC
 N  L  E  K  T  T  A  A  L  S  I  L  P  G  I  G  S  V  M  G  315

1030      1040      1050      1060      1070      1080
ATTGCAGACGGTGCCGTTCACCACAATACAGAAGAGATAGTGGCACAATCAATAGCTTTA
 I  A  D  G  A  V  H  H  N  T  E  E  I  V  A  Q  S  I  A  L  335

1090      1100      1110      1120      1130      1140
TCGTCTTTAATGGTTGCTCAAGCTATTCCATTGGTAGGAGAGCTAGTTGATATTGGTTTC
 S  S  L  M  V  A  Q  A  I  P  L  V  G  E  L  V  D  I  G  F  355

1150      1160      1170      1180      1190      1200
GCTGCATATAATTTTGTAGAGAGTATTATCAATTTATTTCAAGTAGTTCATAATTCGTAT
 A  A  Y  N  F  V  E  S  I  I  N  L  F  Q  V  V  H  N  S  Y  375

1210      1220      1230      1240      1250      1260
AATCGTCCCGCGTATTCTCCGGGGCATAAAACGCAACCATTTCTTCATGACGGGTATGCT
 N  R  P  A  Y  S  P  G  H  K  T  Q  P  F  L  H  D  G  Y  A  395

1270      1280      1290      1300      1310      1320
GTCAGTTGGAACACTGTTGAAGATTCGATAATCCGAACTGGTTTTCAAGGGGAGAGTGGG
 V  S  W  N  T  V  E  D  S  I  I  R  T  G  F  Q  G  E  S  G  415

1330      1340      1350      1360      1370      1380
CACGACATAAAAATTACTGCTGAAAATACCCCGCTTCCAATCGCGGGTGTCCTACTACCG
 H  D  I  K  I  T  A  E  N  T  P  L  P  I  A  G  V  L  L  P  435

1390      1400      1410      1420      1430      1440
ACTATTCCTGGAAAAGCTGGACGTTAATAAGTCCAAGACTCATATTTCCGTAAATGGTCGG
 T  I  P  G  K  L  D  V  N  K  S  K  T  H  I  S  V  N  G  R  455

1450      1460      1470      1480      1490      1500
AAAATAAGGATGCGTTGCAGAGCTATAGACGGTGATGTAACTTTTTTGTCGCCCTAAATCT
 K  I  R  M  R  C  R  A  I  D  G  D  V  T  F  C  R  P  K  S  475

1510      1520      1530      1540      1550      1560
CCTGTTTATGTTGGTAATGGTGTGCATGCGAATCTTCACGTGGCATTTCACAGAAGCAGC
 P  V  Y  V  G  N  G  V  H  A  N  L  H  V  A  F  H  R  S  S  495

1570      1580      1590      1600      1610      1620
TCGGAGAAAATTCATTCTAATGAAATTTCGTCGGATTCCATAGGCGTTCTTGGGTACCAG
 S  E  K  I  H  S  N  E  I  S  S  D  I  G  V  L  G  Y  Q  515

1630      1640      1650      1660      1670      1680
AAAACAGTAGATCACACCAAGGTTAATTCTAAGCTATCGCTATTTTTTGAAATCAAAAGC
 K  T  V  D  H  T  K  V  N  S  K  L  S  L  F  F  E  I  K  S  535

1690
TGA
 *
```

FIG. 5

```
                10         20         30         40         50         60
        ATGTCCCCTATACTAGGTTATTGGAAAATTAAGGGCCTTGTGCAACCCACTCGACTTCTT
         M  S  P  I  L  G  Y  W  K  I  K  G  L  V  Q  P  T  R  L  L 70         80         90        100        110        120
        TTGGAATATCTTGAAGAAAAATATGAAGAGCATTTGTATGAGCGCGATGAAGGTGATAAA
         L  E  Y  L  E  E  K  Y  E  E  H  L  Y  E  R  D  E  G  D  K 130        140        150        160        170        180
        TGGCGAAACAAAAAGTTTGAATTGGGTTTGGAGTTTCCCAATCTTCCTTATTATATTGAT
         W  R  N  K  K  F  E  L  G  L  E  F  P  N  L  P  Y  Y  I  D 190        200        210        220        230        240
        GGTGATGTTAAATTAACACAGTCTATGGCCATCATACGTTATATAGCTGACAAGCACAAC
         G  D  V  K  L  T  Q  S  M  A  I  I  R  Y  I  A  D  K  H  N 250        260        270        280        290        300
        ATGTTGGGTGGTTGTCCAAAAGAGCGTGCAGAGATTTCAATGCTTGAAGGAGCGGTTTTG
         M  L  G  G  C  P  K  E  R  A  E  I  S  M  L  E  G  A  V  L 310        320        330        340        350        360
        GATATTAGATACGGTGTTTCGAGAATTGCATATAGTAAAGACTTTGAAACTCTCAAAGTT
         D  I  R  Y  G  V  S  R  I  A  Y  S  K  D  F  E  T  L  K  V 370        380        390        400        410        420
        GATTTTCTTAGCAAGCTACCTGAAATGCTGAAAATGTTCGAAGATCGTTTATGTCATAAA
         D  F  L  S  K  L  P  E  M  L  K  M  F  E  D  R  L  C  H  K 430        440        450        460        470        480
        ACATATTTAAATGGTGATCATGTAACCCATCCTGACTTCATGTTGTATGACGCTCTTGAT
         T  Y  L  N  G  D  H  V  T  H  P  D  F  M  L  Y  D  A  L  D 490        500        510        520        530        540
        GTTGTTTTATACATGGACCCAATGTGCCTGGATGCGTTCCCAAAATTAGTTTGTTTTAAA
         V  V  L  Y  M  D  P  M  C  L  D  A  F  P  K  L  V  C  F  K 550        560        570        580        590        600
        AAACGTATTGAAGCTATCCCACAAATTGATAAGTACTTGAAATCCAGCAAGTATATAGCA
         K  R  I  E  A  I  P  Q  I  D  K  Y  L  K  S  S  K  Y  I  A
```

FIG. 6

```
         610       620       630       640       650       660
TGGCCTTTGCAGGGCTGGCAAGCCACGTTTGGTGGTGGCGACCATCCTCCAAAATCGGAT
 W  P  L  Q  G  W  Q  A  T  F  G  G  G  D  H  P  P  K  S  D 670       680       690       700       710       720
CTGATCGAAGGTCGTGGGATCCCCGCGTATTCTCCGGGGCATAAAACGCAACCATTTCTT
 L  I  E  G  R  G  I  P  A  Y  S  P  G  H  K  T  Q  P  F  L 730       740       750       760       770       780
CATGACGGGTATGCTGTCAGTTGGAACACTGTTGAAGATTCGATAATCCGAACTGGTTTT
 H  D  G  Y  A  V  S  W  N  T  V  E  D  S  I  I  R  T  G  F 790       800       810       820       830       840
CAAGGGGAGAGTGGGCACGACATAAAAATTACTGCTGAAAATACCCCGCTTCCAATCGCG
 Q  G  E  S  G  H  D  I  K  I  T  A  E  N  T  P  L  P  I  A 850       860       870       880       890       900
GGTGTCCTACTACCGACTATTCCTGGAAAGCTGGACGTTAATAAGTCCAAGACTCATATT
 G  V  L  L  P  T  I  P  G  K  L  D  V  N  K  S  K  T  H  I 910       920       930       940       950       960
TCCGTAAATGGTCGGAAAATAAGGATGCGTTGCAGAGCTATAGACGGTGATGTAACTTTT
 S  V  N  G  R  K  I  R  M  R  C  R  A  I  D  G  D  V  T  F 970       980       990      1000      1010      1020
TGTCGCCCTAAATCTCCTGTTTATGTTGGTAATGGTGTGCATGCGAATCTTCACGTGGCA
 C  R  P  K  S  P  V  Y  V  G  N  G  V  H  A  N  L  H  V  A 1030      1040      1050      1060      1070      1080
TTTCACAGAAGCAGCTCGGAGAAAATTCATTCTAATGAAATTTCGTCGGATTCCATAGGC
 F  H  R  S  S  S  E  K  I  H  S  N  E  I  S  S  D  S  I  G 1090      1100      1110      1120      1130      1140
GTTCTTGGGTACCAGAAAACAGTAGATCACACCAAGGTTAATTCTAAGCTATCGCTATTT
 V  L  G  Y  Q  K  T  V  D  H  T  K  V  N  S  K  L  S  L  F 1150      1160
TTTGAAATCAAAAGCTGA
 F  E  I  K  S  *
```

ANTICANCER AGENT

This Application is the U.S. National Stage Application under 35 U.S.C. 371 of PCT International Application PCT/JP/2005/015135 filed Aug. 19, 2005, which claims benefit from Japanese Patent Application No. 2005-52165 filed Feb. 25, 2005, the complete disclosures of which, including any and all sequence listings, are incorporated herein by reference.

TECHNICAL FIELD

The present invention relates to an antineoplastic agent or an antineoplastic agent composition, a method for treating a cancer and a kit for treating the cancer, which are effective for treating various cancers such as ovarian cancers, breast cancers, prostate cancers, uterus cancers, lung cancers, pancreatic cancers, stomach cancers, cancers of the colon and rectum and glioblastoma.

BACKGROUND ART

Various therapeutic methods and therapeutic drugs for malignant tumors have been developed, but sufficient therapeutic effects often have not been able to be obtained yet. Antineoplastic agents such as taxol, carboplatin and irinotecan are effective, but their side effects are strong, and thus, reduction of the side effect has been desired.

Meanwhile, HB-EGF is known to be a cell growth factor of the EGF family and as a molecule which is essential for formation and regeneration process of a body as well as is involved in occurrence of vascular stenosis and arteriosclerosis (see, e.g., Non-patent literature 1). This molecule is synthesized as a membrane bound precursor (proHB-EGF), and is cleaved on the cell surface with protease to produce the soluble form HB-EGF. A growth promoting action is observed in the soluble form whereas a growth inhibitory action is observed in the membrane-anchored form. Thus, HB-EGF seems to serve for formation and maintenance of tissues by appropriately using the soluble form or the membrane-anchored form as the situation demands.

HB-EGF is bound to EGF receptor (EGFR) (Her1) and Her4 (ErbB-4) in the EGFR family and activates them. However, members (Her1, Her2, Her3 and Her4) in the EGFR family can form heterodimers in all combinations as well as form homodimers. Thus, consequently, HB-EGF can activate all molecules in the EGFR family. HB-EGF is expressed in various tissues, and appears to act in broad cells and tissues, and is reported to promote well the growth of fibroblasts, smooth muscle cells and keratinocytes (see e.g., Non-patent literature 2).

HB-EGF is synthesized as the membrane bound precursor (proHB-EGF) as described above, and proHB-EGF is composed of, from an N terminus, a signal sequence, a prosequence, a heparin binding domain, an EGF-like domain, a juxtamembrane domain, a transmembrane domain and a cytoplasmic domain (FIG. 1). This proHB-EGF becomes the soluble form by being cleaved with protease (ectodomain shedding) at a portion indicated by an arrow in the figure. It has been proposed that the ectodomain shedding of proHB-EGF is stimulated by a pathway in which lysophosphatidic acid (LPA) activates Ras-Raf-MEK pathway through a G protein-coupled receptor or a pathway in which phorbol ester activates PKC (see e.g., Non-patent literature 3).

A function that the soluble form HB-EGF is bound to EGFR and facilitates phosphorylation of EGFR is present in the EGF-like domain (see e.g., Non-patent literature 1).

It has been known that diphtheria toxin is a protein having a molecular weight of about 59,000 produced by diphtheria *bacillus* and is bound to the membrane-anchored form precursor (proHB-EGF) of HB-EGF as the receptor (see e.g., Non-patent literature 4). Also, a mutant such as CRM197 of diphtheria toxin is known as an inhibitor of the soluble form HB-EGF (see e.g., Non-patent literature 5). Database information of diphtheria toxin is available for its gene in EMBL; K01722, its amino acid sequence in SWISS-PROT; P00588 and its three dimensional structure in PDB; 1MDT or 1×DT. A phage lysogenized in a diphtheria bacilli encodes the gene of diphtheria toxin.

Diphtheria toxin is a simple protein composed of 535 amino acid residues (the amino acid sequence [SEQ ID NO:1] of diphtheria toxin and a base sequence [SEQ ID NO:2] of the gene encoding it are shown in FIGS. 2 and 3, and italic letters represent the signal sequence). Diphtheria toxin can be separated into fragment A and fragment B by treating with a reducing agent (FIG. 4). According to conformational analyses, the fragment B is further divided into two domains. For the function of each domain, a catalytic domain corresponding to the fragment A (amino acid numbers 1 to 193 when the signal sequence is excluded) has an ADP ribosylation activity, a transmembrane domain (amino acid numbers 194 to 378 when the signal sequence is excluded) corresponding to an N terminal half of the fragment B has a nature to form a channel in an endosome membrane, and a receptor-binding domain (amino acid numbers 386 to 535 when the signal sequence is excluded) corresponding to a C terminal half of the fragment B has an activity to bind to a diphtheria toxin receptor on the cell surface.

The fragment A (catalytic domain) of diphtheria toxin has the action to ADP-ribosylate EF-2 (elongation factor 2) in the presence of NAD, thereby inhibiting protein synthesis. Therefore, in order to exert the toxicity of diphtheria toxin, the fragment A must enter in cytoplasm.

In the mechanism in which the fragment A enters in the cytoplasm, the receptor-binding domain in the fragment B is bound to proHB-EGF which is the receptor on the cell surface to internalize diphtheria toxin by endocytosis, then the transmembrane domain is inserted in the endosome membrane in the endosome, and finally the fragment A is released in the cytoplasm by passing through the endosome to inactivate EF-2 there (see e.g., Non-patent literature 6).

To exert the toxicity of diphtheria toxin, both the fragments A and B are necessary. Therefore, if either the fragment has a mutation, a protein having no toxicity of diphtheria toxin can be generated.

In diphtheria toxin, the detoxified mutant such as CRM197 having the mutation in the catalytic domain has been isolated.

Meanwhile, the mutant of diphtheria toxin has the activity to inhibit the binding between HB-EGF and EGFR because diphtheria toxin is bound to the EGF-like domain of the soluble form HB-EGF. The receptor-binding domain of diphtheria toxin is involved in this binding. It has been reported that Lys at position 516 and Phe at position 530 in diphtheria toxin are important for the binding to HB-EGF (see e.g., Non-patent literature 7). A crystal structure of a complex composed of diphtheria toxin and the EGF domain of HB-EGF has been analyzed, and the important amino acid residues for binding to HB-EGF have been reported to be between positions 381 and 535 (see e.g., Non-patent literature 8).

This way, it has been observed that diphtheria toxin mutant is bound to HB-EGF and inhibits the activity of HB-EGF. Recently, it has been attempted to use diphtheria toxin mutant as the therapeutic agent for the cancer by targeting HB-EGF for cancer therapy, but the attempt has not come into practical use yet (Patent document 1, Non-patent literature 9).

Patent document 1: JP 2004-155776-A;
Non-patent literature 1: Mekata E. et al, "Idenshi Igaku" Vol. 5, No. 2, P. 131-134, 2001, Medical Do Co., Ltd.;
Non-patent literature 2: Higashiyama, S. et al., J. Cell Biol., 122: 933-940, 1993;
Non-patent literature 3: Prenzel, N. et al., Nature 402: 884-888, 1999;
Non-patent literature 4: J. G. Naglich et al., Cell 69: 1051-1061, 1992;
Non-patent literature 5: T. Mitamura et al., J. Biol. Chem., 270: 1015, 1995;
Non-patent literature 6: T. Umata et al., J. Biol. Chem., 273: 8351, 1998;
Non-patent literature 7: Shen, H S et al., J. Biol. Chem., 269: 29077-29084, 1994;
Non-patent literature 8: Gordon V L et al., Molecular Cell 1: 67-78, 1997;
Non-patent literature 9: Miyamoto, S. et al., Cancer Res., 64: 5720-5727, 2004.

DISCLOSURE OF THE INVENTION

Problems to be Solved by the Invention

The present invention makes it a task to solve the above conventional various problems and accomplish the following objects. That is, it is an object of the present invention to provide an antineoplastic agent and a method for treating cancers, effective for the treatment of malignant tumors with no side effect.

Means for Solving the Problems

The present inventors have obtained a finding that a synergistic effect is obtained by using a diphtheria toxin mutant in combination with one or two or more selected from the group consisting of paclitaxel (taxol), carboplatin, irinotecan and derivatives thereof, and led to the present invention.

That is, procedures to solve the above problems of the present invention are as follows.

[1] An antineoplastic agent characterized by combining (a) at least one of paclitaxel, carboplatin, irinotecan and derivatives thereof with (b) a protein which is a diphtheria toxin mutant having an activity to inhibit a binding between HB-EGF and EGFR and substantially not having toxicity of diphtheria toxin.

[2] The antineoplastic agent according to [1] characterized in that the protein comprises at least a receptor-binding domain with no mutation in an amino acid sequence of diphtheria toxin.

[3] The antineoplastic agent according to [1] wherein the protein is a protein composed of an amino acid sequence having one or more amino acid deletions, substitutions or additions in the amino acid sequence of diphtheria toxin.

[4] The antineoplastic agent according to [1] wherein the protein is either CRM197 or DT52E148K.

[5] The antineoplastic agent according to [1] wherein (a) at least one of paclitaxel, carboplatin, irinotecan and the derivatives thereof is combined with (b) the protein which is diphtheria toxin mutant having the activity to inhibit the binding between HB-EGF and EGFR and substantially not having toxicity of diphtheria toxin in amounts in which both independently have no sufficient anti-cancer action.

[6] A method for treating cancers characterized by administering (a) at least one of paclitaxel, carboplatin, irinotecan and derivatives thereof in combination with (b) a protein which is a diphtheria toxin mutant having an activity to inhibit a binding between HB-EGF and EGFR and substantially not having toxicity of diphtheria toxin.

[7] The method according to [6] wherein (a) at least one of paclitaxel, carboplatin, irinotecan and the derivatives thereof and (b) the protein which is diphtheria toxin mutant having the activity to inhibit the binding between HB-EGF and EGFR and substantially not having the toxicity of diphtheria toxin are administered in amounts in which both independently have no sufficient anticancer action but the anticancer action is elicited by combining the both.

[8] A kit for treating cancers, composed of (a) at least one of paclitaxel, carboplatin, irinotecan and derivatives thereof and (b) a protein which is a diphtheria toxin mutant having an activity to inhibit a binding between HB-EGF and EGFR and substantially not having toxicity of diphtheria toxin.

[9] The kit according to [8] characterized by comprising (a) at least one of paclitaxel, carboplatin, irinotecan and the derivatives thereof and (b) the protein which is diphtheria toxin mutant having the activity to inhibit the binding between HB-EGF and EGFR and substantially not having the toxicity of diphtheria toxin in amounts in which both independently have no sufficient anticancer action but the anticancer action is elicited by combining the both.

[10] An antineoplastic agent composition comprising (a) at least one of paclitaxel, carboplatin, irinotecan and derivatives thereof and (b) a protein which is a diphtheria toxin mutant having an activity to inhibit a binding between HB-EGF and EGFR and substantially not having toxicity of diphtheria toxin.

EFFECTS OF THE INVENTION

According to the present invention, it is possible to provide the antineoplastic agent or the antineoplastic agent composition, the method for treating the cancer and the kit for treating the cancer, which are effective for the treatment of the malignant tumors such as ovarian cancers, breast cancers, prostate cancers, uterus cancers, lung cancers, pancreatic cancers, stomach cancers, cancers of the colon and rectum and glioblastoma.

BRIEF DESCRIPTION OF THE DRAWINGS

FIG. 2 is a view showing an amino acid sequence (Residues 1-300 of SEQ ID NO: 1) and a base sequence (Bases 1-900 of SEQ ID NO: 2) of diphtheria toxin;

FIG. 3 is a view showing the amino acid sequence (Residues 301-560 of SEQ ID NO: 1) and the base sequence (Bases 901-1,683 of SEQ ID NO: 2) of diphtheria toxin (sequel to FIG. 2);

FIG. 5 is a view showing an amino acid sequence (Residues 1-200 of SEQ ID NO: 5) and a base sequence (Bases 1-600 of SEQ ID NO: 6) of GST-DT;

FIG. 6 is a view showing the amino acid sequence (Residues 201-385 of SEQ ID NO: 5) and the base sequence (Bases 601-1,158 of SEQ ID NO: 6) of GST-DT (sequel to FIG. 5);

BEST MODES FOR CARRYING OUT THE INVENTION

Figure 1:
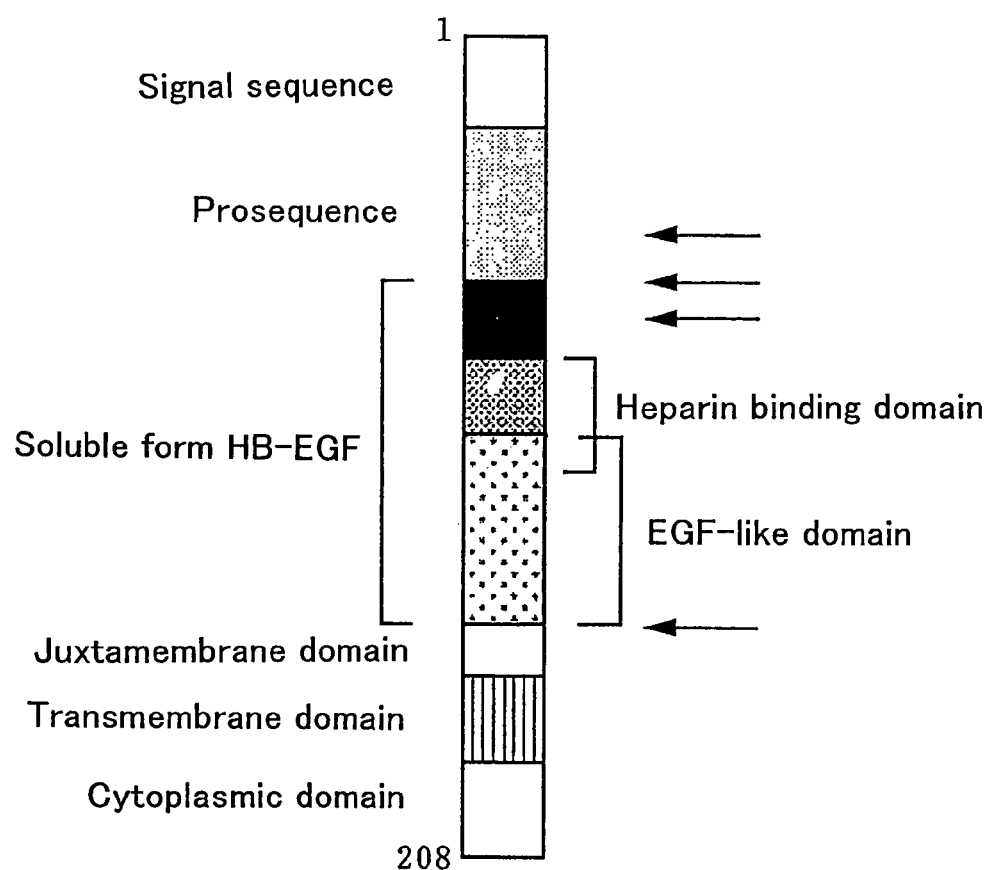
FIG. 1 is a schematic view showing a structure of proHB-EGF.
Figure 4:
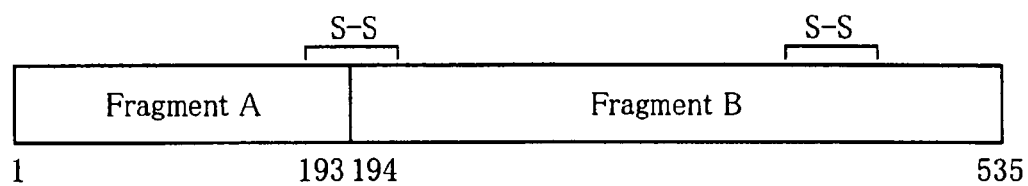
FIG. 4 is a view showing a domain structure of diphtheria toxin.

A first aspect is characterized by combining (a) at least one of paclitaxel, carboplatin, irinotecan and derivatives thereof with (b) a protein which is a diphtheria toxin mutant having an activity to inhibit a binding between HB-EGF and EGFR and substantially not having toxicity of diphtheria toxin. By combining the anticancer agent (a) with the protein (b), an amount of the anticancer agent (a) to be used can be reduced to inhibit side effects and elicit sufficient anticancer actions.

The above diphtheria toxin mutant indicates the protein composed of the amino acid sequence having one or multiple amino acid deletions, substitutions or additions in the amino acid sequence of diphtheria toxin, and is, for example the protein composed of the amino acid sequence having one or more amino acid deletions, substitutions or additions. A signal sequence composed of 25 amino acid residues of diphtheria toxin may or may not be included, and both sequences are included in the scope of the present invention.

A paclitaxel derivative includes docetaxel (taxotale), a carboplatin derivative includes cisplatin, and an irinotecan derivative includes topotecan.

The antineoplastic agent of a second aspect of the present invention uses any of the following proteins (a), (b) and (c) as the above protein:

(a) a protein composed of a portion of diphtheria toxin and comprising at least a receptor-binding domain of diphtheria toxin;

(b) a protein composed of the amino acid sequence having one or more amino acid deletions, substitutions or additions in the amino acid sequence of the protein (a); and (c) a complex protein comprising either the protein (a) or (b).

The above protein refers to one which is the portion of diphtheria toxin or the mutant thereof or the complex protein comprising such a protein and holds the receptor-binding domain.

Here, the toxicity of diphtheria toxin means that diphtheria toxin is bound to the receptor on the cell surface, enters into a cell and a protein synthesis function of the cell is inhibited by an activity of the fragment A to ADP-ribosylate EF-2 (peptide elongation factor 2), and can be easily determined by degrees of the protein synthesis inhibition. That is, a certain amount of diphtheria toxin is added to cultured cells, which are then cultured for about 2 to 8 hours. Subsequently, the cells are cultured in the presence of a radioactive amino acid for a short time, and then the radioactive amino acid incorporated in the protein is quantified.

Specifically, Vero cells ($1 \times 10^5$ cells) are seeded in a 24-well plate, and cultured in a $CO_2$ incubator for 16 hours. After confirming that the cells sufficiently adhere to the plate, each well is washed once with cold PBS (150 mM NaCl, 2.7 mM KCl 10 mM phosphate buffer, pH 7.2). At that time, the liquid is carefully added and discarded so that the cells are not detached. Then, 0.5 mL of medium for assay containing serum is added. As the medium for the assay, one in which a concentration of leucine has been reduced to about 1/10 compared with the ordinary medium is used. This is because an uptake efficiency of [$^3$H]-leucine added later is increased. But, Ham's F12 medium contains a less content of leucine, and thus this can also be used as the medium for the assay. The serum is added at the concentration typically used.

Subsequently, various concentrations of diphtheria toxin are added, and the cells are cultured in the $CO_2$ incubator for 2 to 5 hours. Then, 10 µL, of 3.7 MBq/mL [$^3$H]-leucine is added, and the culture is continued for an additional one hour.

The medium is discarded, the well is washed once with PBS, the cells are lysed with 0.5 mL of 0.1 M NaOH, and a cell lysate is collected in a tube. The well is washed again with 0.5 mL of 0.1 M NaOH, and the solution is collected in the same tube.

To this, 0.5 mL of 20% trichloroacetic acid solution is added, which is then agitated on a Vortex mixer. A produced precipitate is trapped with a glass filter, and the filter is further washed with 5% trichloroacetic acid solution.

Finally, the filter is washed with 100% ethanol, and dried.

The filter is immersed in toluene PPO scintillator, and a radioactivity trapped in the filter is measured by a liquid scintillation counter. A value in a sample in which diphtheria toxin was not added is measured, this value is made 100%, and a value in a sample in which the toxin was added is calculated as %.

The protein substantially not having the toxicity of diphtheria toxin refers to the protein in which the toxicity of diphtheria toxin has been detoxified or attenuated to an extremely low level, and in the present invention, refers to those having no significant difference from the value in the sample in which diphtheria toxin has not been added or the sample in which diphtheria toxin mutant not having the catalytic domain has been added when the toxicity is measured in the above Vero cell system using diphtheria toxin at a concentration of 1 ng/mL. For the significant difference, it is preferable that there is no significant difference at significant level 5% in t-test, it is more preferable that there is no significant difference at significant level 1%, and it is still more preferable that there is no significant difference at significant level 0.1%.

But, in the mutants such as CRM197 and DT52E148K described to have no toxicity of diphtheria toxin until now, it has been proved that the extremely faint toxicity (e.g., about $10^{-10}$ in CRM197 compared with wild type diphtheria toxin) remains (Patent document 1). The mutants having such a faint toxicity are not excluded from the present invention. The toxicity level of diphtheria toxin is preferably the same as or lower than that of CRM197 in terms of eliminating the side effect by the toxicity of diphtheria toxin and increasing the safety.

The toxicity of diphtheria toxin can be controlled by mutating the catalytic domain essential for ADP-ribosylating the peptide elongation factor-2 or deleting a part or all of the catalytic domain.

The function of the mutated catalytic domain can be exactly examined by directly measuring the ADP ribosylation activity. The ADP ribosylation activity can be directly measured by adding the fragment A or the protein (mutated catalytic domain) in which the ADP ribosylation activity is to be measured and NAD labeled with a radioisotope to isolated and purified EF-2, ADP-ribosylating EF-2 in vitro and measuring the radioactivity incorporated into EF-2.

Specifically, Tris buffer (pH 7.8) at a final concentration of 20 mM, 1 mM MTT (dithiothreitol) 0.1 to 1 µg/mL of the fragment A or 0.1 to 100 µg/mL of the protein in which the ADP ribosylation activity is to be measured are added to a rabbit reticulocyte EF-2 fraction obtained by the method described in the following reference, Moynihan, M. R. and Pappenheimer, A. M. Jr. Infect. Immun., 32: 575-582, 1981, further [$^{32}$P] NAD at a final activity of 370 KBq/mL (about 740 GBq/mM) is added thereto and mixed, and the mixture is reacted at 37° C. for 10 minutes.

The same volume of 10% trichloroacetic acid solution is added to the reaction solution to precipitate a protein, a resulting precipitate is trapped in a glass filter, and the filter is further washed with 5% trichloroacetic acid solution.

Finally, the filter is washed with 100% ethanol and dried.

The filter is immersed in toluene PPO scintillator, and the radioactivity trapped in the filter is measured by the liquid scintillation counter.

The measured radioactivity indicates the degree of the ADP ribosylation activity, and the relative activity of the ADP ribosylation in the mutated protein can be determined based on the radioactivity using the unmutated fragment A.

According to more detailed investigation of the present inventors based on domain information, it has been found that including the amino acid sequence from positions 378 to 535 corresponding to the portion comprising the receptor-binding domain is only necessary for the characteristic of having the activity to inhibit the binding between the soluble form HB-EGF and EGFR. That is, a gene in which the sequence from the positions 378 to 535 of diphtheria toxin had been fused to GST (gluthathione-S-transferase) was made, and this was expressed in *Escherichia coli* to produce a fusion protein (GST-DT) having the above structure. GST-DT inhibited the binding of the $^{125}$I-labeled diphtheria toxin to HB-EGF in a dose dependent manner. It was found by the degree of the inhibition that GST-DT was bound to HB-EGF with similar strength to that of diphtheria toxin. Therefore, it was found that the sequence required for the binding was the sequence from the positions 378 to 535, i.e., the portion comprising the receptor-binding domain.

Whether having the activity to inhibit the binding between HB-EGF and EGFR can be determined by the above inhibition experiment in the binding of the aforementioned $^{125}$I-labeled diphtheria toxin to HB-EGF.

Thus, the protein having the activity to inhibit the binding between HB-EGF and EGFR and substantially not having the toxicity of diphtheria toxin can be obtained by making a diphtheria toxin mutant protein having the mutation in the catalytic domain with holding the receptor-binding domain, or a protein which is a portion of diphtheria toxin obtained by deleting a part or all of the catalytic domain with holding the receptor-binding domain of diphtheria toxin.

Examples of such a mutant include CRM197, DT52E148K and GST-DT. These do not have the toxicity of diphtheria toxin substantially, and inhibit the binding of HB-EGF to EGFR. CRM197 is the mutant obtained by mutating Gly to Glu at position 52 when counted without including the signal sequence composed of 25 amino acid residues. DT52E148K is the mutant obtained by mutating Glu to Lys at position 148 in addition to the above mutation when counted without including the signal sequence. GST-DT is the protein comprising the positions 378 to 535 of diphtheria toxin when counted without including the signal sequence of diphtheria toxin. The amino acid sequence (first 25 amino acid residues represent the signal sequence) for CRM197 and the base sequence of the gene encoding it are shown in SEQ ID NOS:3 and 4, respectively. The amino acid sequence (SEQ ID NO:5) for GST-DT and the base sequence (SEQ ID NO:6) of the gene encoding it are shown in FIGS. 5 and 6, respectively.

CRM197 has been already reported to not have the toxicity of diphtheria toxin, i.e., not have the ADP ribosylation activity (T. Uchida and A. M. Pappenheimer Jr. Science 175: 901-903, 1972). A 148K mutant having the mutation at position 148E has been known to have only an extremely faint activity (J. T. Barbieri and R. J. Collier, Infect. Immun., 55: 1647-1651, 1987). DT52E148K which is a double mutant having the 148K mutation in addition to CRM197 which is the 52E mutant is preferable as the safer mutant. The toxicity of these mutants was identified to have no significant difference from the value of the sample in which diphtheria toxin had not been added in the aforementioned protein synthesis inhibition experiment. It is obvious from completely lacking the catalytic domain that GST-DT has no toxicity of diphtheria toxin.

SEQ ID NO: 3
MSRKLFASILIGALLGIGAPPSAHAGADDVVDSSKSFVMENFSSYHGT

KPGYVDSIQKGIQKPKSGTQGNYDDDWKEFYSTDNKYDAAGYSVDNEN

PLSGKAGGVVKVTYPGLTKVLALKVDNAETIKKELGLSLTEPLMEQVG

TEEFIKRFGDGASRVVLSLPFAEGSSSVEYINNWEQAKALSVELEINF

ETRGKRGQDAMYEYMAQACAGNRVRRSVGSSLSCINLDWDVIRDKTKT

KIESLKEHGPIKNKMSESPNKTVSEEKAKQYLEEFHQTALEHPELSEL

KTVTGTNPVFAGANYAAWAVNVAQVIDSETADNLEKTTAALSILPGIG

SVMGIADGAVHHNTEEIVAQSIALSSLMVAQAIPLVGELVDIGFAAYN

FVESIINLFQVVHNSYNRPAYSPGHKTQPFLHDGYAVSWNTVEDSIIR

TGFQGESGHDIKITAENTPLPIAGVLLPTIPGKLDVNKSKTHISVNGR

KIRMRCRAIDGDVTFCRPKSPVYVGNGVHANLHVAFHRSSSEKIHSNE

ISSDSIGVLGYQKTVDHTKVNSKLSLFFEIKS

A fragment containing the receptor-binding domain can be made by synthesizing a DNA sequence of the receptor-binding domain by PCR using a gene (Pβ197) encoding CRM197 incorporated in a plasmid as a template, inserting this in multicloning site of an expression vector (pGEX-3X, pQE-30) for synthesizing a GST fusion protein or a histidine tag, incorporating a resulting plasmid in *Escherichia coli* and synthesizing the gene encoded by the plasmid in *Escherichia coli*.

The mutant having the mutation in the catalytic domain can be made as follows. A CRM197 region is synthesized by PCR using the gene (Pβ197) encoding CRM197 incorporated in the plasmid as the template, and using a portion to be mutated as a primer. The primer is synthesized by introducing a point mutation so as to have the mutation, and used. The synthesized DNA can be introduced into a gene expression vector (pET-22b) for *Escherichia coli*, and *Escherichia coli* is transfected with the vector to express the mutant in *Escherichia coli*.

The antineoplastic agent of the present invention can be used for the treatment of malignant tumors in broad range such as ovarian cancers, breast cancers, prostate cancers, cancers of the uterine cervix, cancers of the uterine body, thyroid cancers, lung cancers, pancreatic cancers, stomach cancers, cancers of the colon and rectum and glioblastoma, and preferably can be used for the malignant tumors expressing HB-EGF. The preferable cancers subjected to the treatment are breast cancers, prostate cancers, pancreatic cancers, stomach cancers, cancers of the colon and rectum, ovarian cancers, glioblastoma, cancers of the uterine body and cancers of the uterine cervix.

In the antineoplastic agent of the present invention, the above active ingredient can be directly formulated or can be formulated in combination with a pharmaceutically acceptable carrier for pharmaceuticals.

The antineoplastic agent can be administered orally or parenterally (e.g., intravenous, intramuscular, intraperitoneal, subcutaneous or intradermal injection, intrarectal administration, permucosal administration, administration via respiratory tract). When applied to the malignant tumor such as ovarian cancer intraperitoneally seeded, it is preferable in terms of being directly transported by cancer cells to administer by intraperitoneal injection.

Pharmaceutical compositions suitable for the oral administration include, for example, tablets, granules, capsules, powders, solutions, suspensions and syrups. The pharmaceutical compositions suitable for the parenteral administration include, for example, injectable agents, drops, suppositories and percutaneous absorbing agents, but the formulation is not limited thereto.

Types of additives for the formulations used for producing the antineoplastic agent are not particularly limited and can be appropriately selected by those skilled in the art. For example, excipients, disintegrants and disintegrant aids, binders, lubricants, coating agents, bases, solubilizers and solubilizer aids, dispersants, suspending agents, emulsifiers, buffers, antioxidants, preservatives, tonicity agents, pH adjusters, solubilizers and stabilizers can be used. Individual specific ingredients used for these purposes are well known to those skilled in the art.

As the additives for the formulations usable for preparing the formulations for the oral administration, for example, the excipients such as glucose, lactose, D-mannitol, starch or crystalline cellulose; the disintegrants and disintegrant aids such as carboxymethylcellulose, starch and calcium carboxymethylcellulose; the binders such as hydroxypropylcellulose, hydroxypropylmethylcellulose, polyvinyl pyrrolidone or gelatin; the lubricants such as magnesium stearate and talc; the coating agents such as hydroxypropylmethylcellulose, saccharose, polyethylene glycol or titanium oxide; and the bases such as Vaseline, liquid paraffin, polyethylene glycol, gelatin, kaolin, glycerine, purified water or hard fat, and the like can be used.

As the additives for the formulations usable for preparing the formulations for the injection or drip infusion, the solubilizers and solubilizer aids such as injectable distilled water, saline or propylene glycol, which are aqueous or can constitute a solubilized type injectable agent in use; the tonicity agents such as glucose, sodium chloride, D-mannitol and glycerine; and the pH adjusters such as inorganic acids, organic acids, inorganic bases or organic bases can be used.

An amount of the active ingredient contained in the antineoplastic agent of the present invention varies depending on a formulation form or an administration route of the antineoplastic agent, can not be defined categorically, but can be typically determined by appropriately selecting from the range of about 0.0001 to 70% in the final formulation.

The antineoplastic agent of the present invention can be administered to mammalian animals including human beings.

The amount of the antineoplastic agent of the present invention to be administered should be appropriately increased or decreased depending on conditions such as patient's age, gender, body weight and symptom, and the administration route. As the amount of the active ingredient per day per adult, the amount of the mutant protein of diphtheria toxin which is one of the active ingredients is preferably in the range of about 1 µg to 30 mg per day per kg body weight.

Paclitaxel is typically administered in an amount of 3.5 to 5.5 mg/kg mainly with a platinum based drug. However, in this administration range, myelosuppression becomes remarkable, and continuation of the treatment becomes sometimes difficult. In particular, for peripheral nerve toxicity, the side effect sometimes appears at an initial administration, and the side effect is irreversible. Thus, the reduction of the amount to be administered is important for not only the reduction of the transient side effect but also the reduction of accumulative side effect. By combining with the mutant protein (in particular, CRM197) of diphtheria toxin, it is possible to reduce the amount of paclitaxel to be administered to one fourth or less. Thus, the combination of paclitaxel with CRM197 is thought to contribute to not only the improvement of clinical effects but also the inhibition of side effect occurrence.

Carboplatin is typically administered in an amount of 10 to 20 mg/kg in combination with a taxane based drug. Carboplatin is the drug which induces the remarkable myelosuppression. In females and elderly people basically having lowered bone marrow functions, the severe myelosuppression is compelled, and the lethal cases with complication of severe infection are often experienced clinically. By combining with the mutant protein (in particular, CRM197) of diphtheria toxin, the amount of carboplatin to be administered is reduced to one fourth or less as is the case with paclitaxel, thereby being capable of obtaining the clinical effect equivalent to or more than that by carboplatin alone. It is sufficiently anticipated to avoid the remarkable myelosuppression by this reduction of the amount to be administered.

Irinotecan is typically administered in an amount of 2 to 3 mg/kg mainly in combination with the platinum based drug or as a single drug. In this administration range, gastrointestinal symptoms including diarrhea frequently appear in addition to the remarkable myelosuppression. In particular, when the diarrhea symptom is severe, even if the effect is clinically observed, discontinuation of the chemotherapy using irinotecan is compelled. Irinotecan is also administered over three weeks, and thus, the treatment with irinotecan is often discontinued due to the myelosuppression. By combining with the mutant protein (in particular, CRM197) of diphtheria toxin, the amount of irinotecan to be administered is reduced to one fourth or less, thereby avoiding the discontinuation of the treatment due to the myelosuppression and the cessation of the treatment due to exacerbation of the diarrhea symptom. Thus, it is possible to obtain the sufficient clinical effect by combining irinotecan with CRM197.

The pharmaceutical in the above amount may be administered once a day, or by dividing into several times. It may also be administered once several days to several weeks, or singly. It can also be administered with a component such as steroid to inhibit the side effect. The mutant protein of diphtheria toxin and at least one of paclitaxel, carboplatin, irinotecan and the derivatives thereof may be administered simultaneously or with a time difference.

EXAMPLES

Examples of the present invention will be described below, but the present invention is not limited to these Examples.

Example 1

<Production of CRM 197 Protein>

A stock of lysogenic bacterium of C7(β197) [available from ATCC (American Type Culture Collection) as C7 (beta197)M1 (No. 39255), diphtheria *bacillus* in which C7 (β197) phage was lysogenized] is cultured, and a bacterial solution in a logarithmic growth phase late stage is added to C—Y medium to which 2% filtrated maltose was added so that an initial $OD_{590}$ value was about 0.05. This OD value corresponds to about $5 \times 10^7$ microbial cells/mL. A flask is placed on a rotary shaker at 200 rpm, and the microbial cells are cultured at 35° C. for 16 to 17 hours. The culture is terminated when the OD value becomes 10 to 15.

The above C—Y medium is prepared as follows. That is, 10 g of casamino acids, 20 g of yeast extract solution and 5 g of $KH_2PO_4$ are dissolved in 1 L of distilled water. After adding 2 mL of 50% $CaCl_2.2H_2O$, pH is adjusted to 7.4. The solution is boiled and then filtrated. Subsequently, 2 mL of Mueller and Miller's solution II (22.5 g of $MgSO_4$, 0.115 g of β-alanine, 0.115 g of nicotinic acid, 7.5 mg of pimelic acid, 1 g of $CuSO_4.5H_2O$, 1 g of $ZnSO_4.5H_2O$, 1 g of $MnCl_2.4H_2O$/100 ml $H_2O$) and 1 mL of Mueller and Miller's solution III (20 g of L-cystine, 20 mL of concentrated hydrochloric acid/100 ml $H_2O$) are added. The C—Y medium was obtained by dispensing each 100 mL and autoclaving it.

The CRM protein is purified as follows.

A culture medium is centrifuged at 10,000 g for 15 minutes. Ammonium sulfate is added to a culture supernatant at a saturation degree of 65%. The mixture is left stand in an ice room for 24 to 48 hours. Precipitates are collected, dissolved in 0.02 M Tris hydrochloride buffer pH 7.2, and dialyzed against the same buffer.

A dialyzed solution is centrifuged to remove insoluble matters, the supernatant is applied on a DE52 column, and eluted with NaCl concentration gradient in 0.02 M Tris hydrochloride buffer pH 7.2. CRM197 is eluted at 0.08 M of NaCl. An eluted solution is saturated to 65% with ammonium sulfate. Precipitates are dissolved in 0.01 M Tris hydrochloride buffer, and equilibrated again. Column elution by applying onto the DE52 column and the precipitation with ammonium persulfate are repeated. Subsequently, the sample is applied to a Sephacryl S-200 and eluted with the solution of HEPES-NaOH, pH 7.2 and 0.15 M NaCl. The eluted CRM197 is applied onto a DeToxi gel to remove LPS-like substances contained in the CRM197 sample, and the resulting CRM197 is used for experiments. For absorbance of CRM197 at 280 nm, 100 corresponds to about 0.67 mg/mL.

(Preparation of Cell Lines)

An ovarian cancer cell line, SKOV-3 and a breast cancer cell line, MDA-MB-231 were obtained from ATCC (American Type Culture Collection).

SK-HB-1 cells were obtained by transfecting SKOV-3 cells with human HB-EGF cDNA incorporated in pRC/CMV vector (Invitrogen). The transfection was performed using LipofectAMINE reagent (Invitrogen) in accordance with a manual attached to the product. The transfected cells were cultured in the medium (RPMI-1640-10FCS) containing 400 μg/mL of G418. Surviving cells were seeded again in a petri dish at low density and a growing colony was picked up to yield SK-HB-1 cells. It was identified that this cell expressed HB-EGF at high level, by adding the $^{125}$I-labeled diphtheria toxin to the cells and comparing the radioactivity of diphtheria toxin bound to the cells with that in SKOV-3 cells.

(Tumorigenicity Experiments Using Nude Mice)

The ovarian cancer cell line, SKOV-3, SK-HB1 and the breast cancer cell line, MDA-MB-231 cultured in RPMI+10% FBS were washed with EDTA/PBS(−), and collected with 0.25% trypsin. The cells were washed twice with RPMI+10% FBS and twice with RPMI (no serum), and 250 μL of cell suspension in RPMI (with serum) at $5 \times 10^6$ cells was inoculated in a dorsal portion of nude mice by subcutaneous injection.

Figure 7:
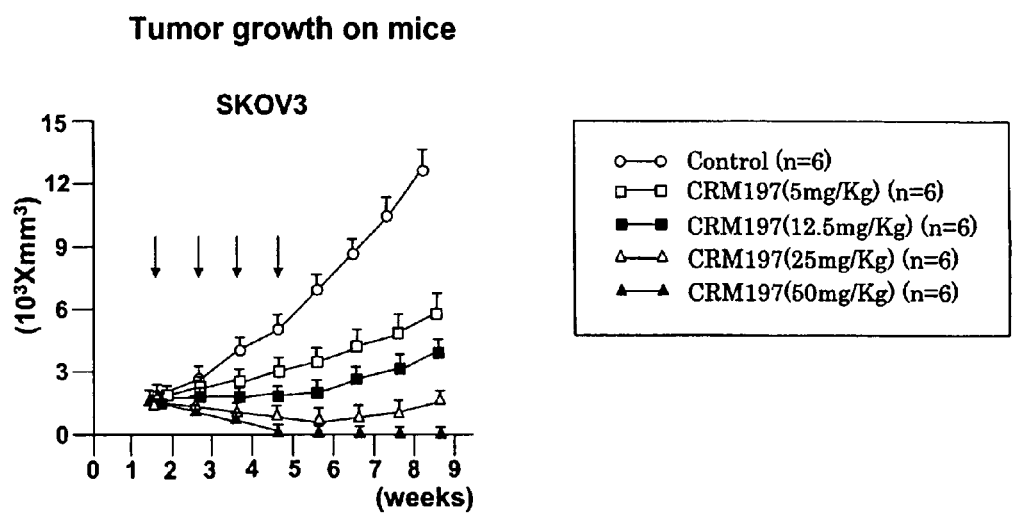
FIG. 7 is a view showing effects by CRM197 administration on tumor growth in nude mice injected with SKOV-3 cells.
Figure 8:
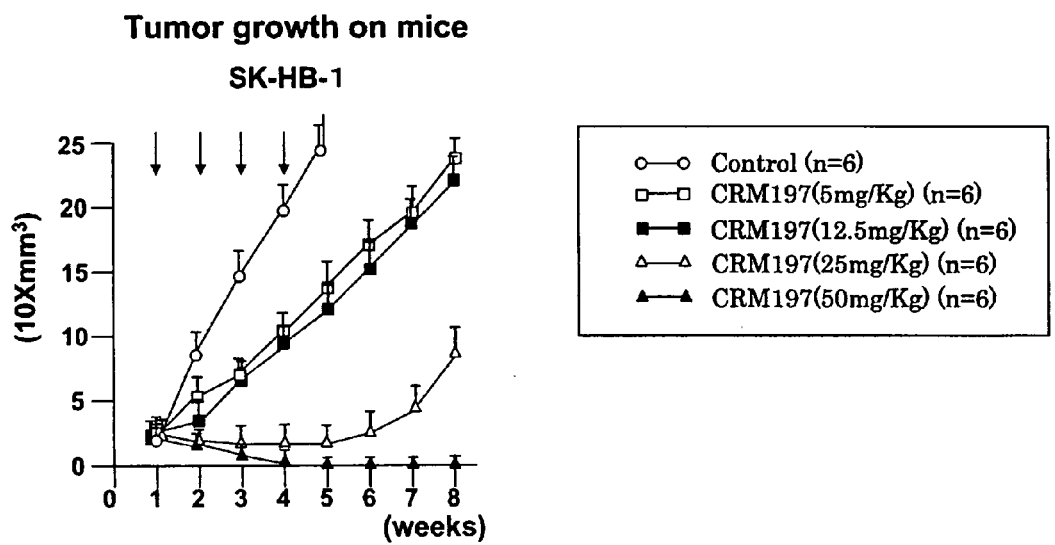
FIG. 8 is a view showing effects by CRM197 administration on tumor growth in nude mice injected with SK-HB1 cells.

In one group of the nude mice, 10 days after inoculating SKOV-3 or SK-HB1 cells, the administration of CRM197 was initiated, and CRM197 was intraperitoneally administered in amounts shown in FIGS. 7 and 8 once a week over 4 weeks. The nude mice to which CRM197 had not been administered were used as controls. Relations between administration time periods and tumor volumes are shown in FIGS. 7 and 8. Here, the tumor volume was obtained by measuring a major axis and a minor axis of the tumor every 3 to 4 days and calculating by Major axis×Minor axis×Minor axis×1/2.

Figure 9:
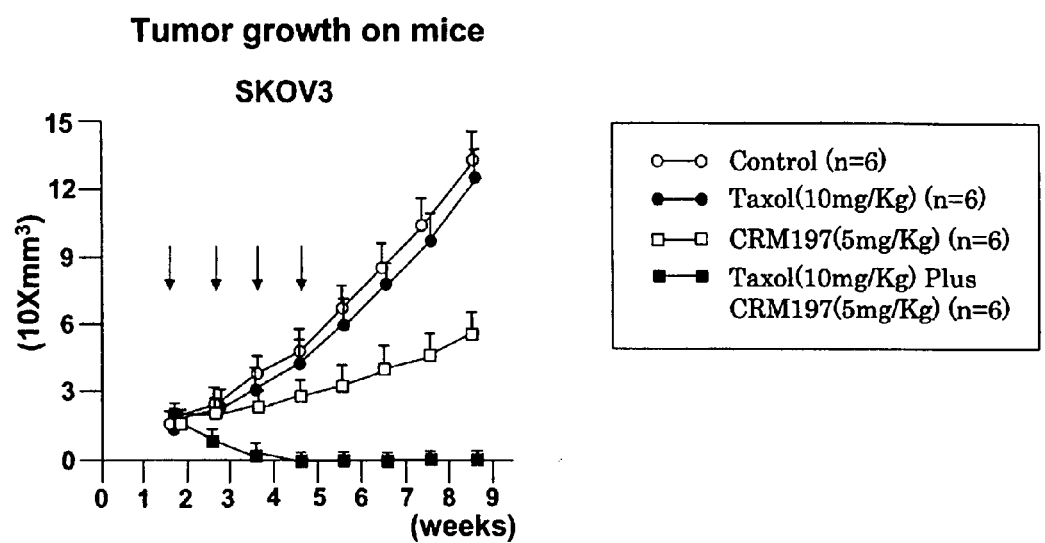
FIG. 9 is a view showing effects by CRM197 and taxol administration on tumor growth in nude mice injected with SKOV-3 cells.
Figure 10:
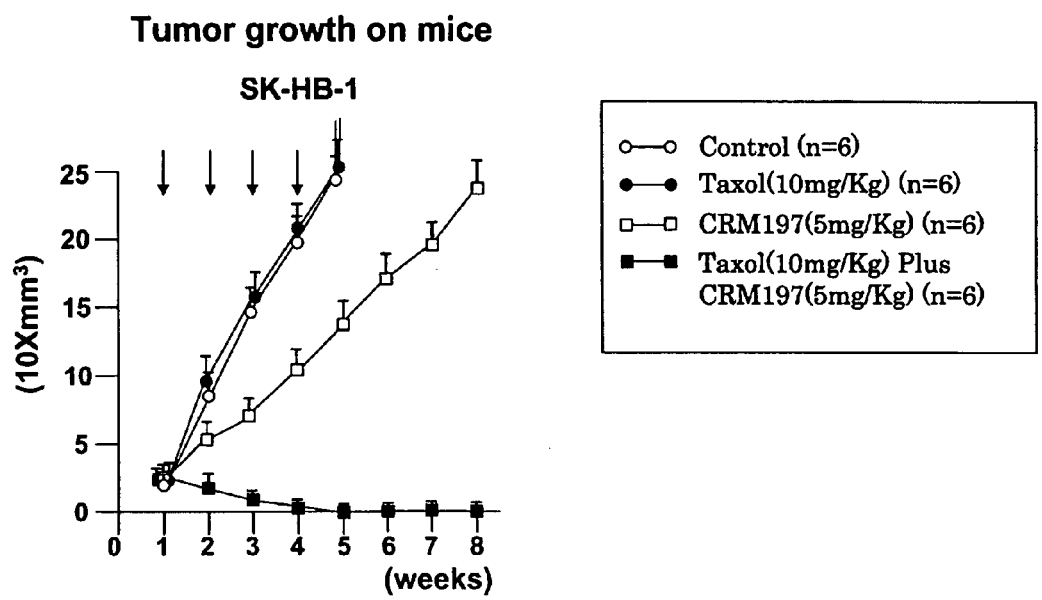
FIG. 10 is a view showing effects by CRM197 and taxol administration on tumor growth in nude mice injected with SK-HB1 cells.
Figure 11:
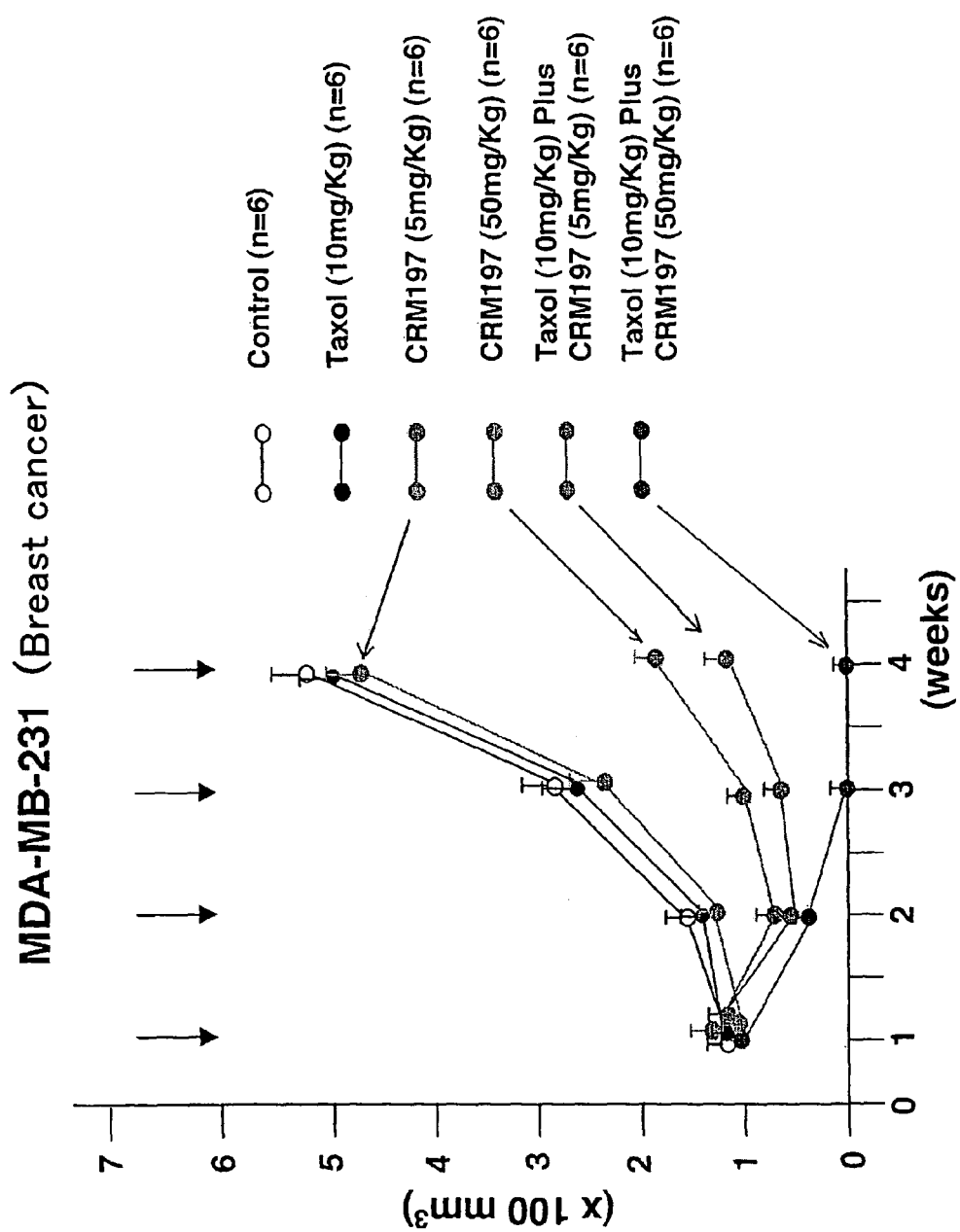
FIG. 11 is a view showing effects by CRM197 and taxol administration on tumor growth in nude mice injected with MDA-MB-231 (breast cancer) cells.

Subsequently, for other groups of the nude mice, 7 days after inoculating SKOV-3 or SK-HB1 or MDA-MB-231 cells, the administration of CRM197 in combination with taxol (Bristol-Myers K.K.) was initiated. Both drugs were intraperitoneally administered in amounts shown in FIGS. 9 to 11 once a week over 4 weeks. The nude mice to which CRM197 and taxol had not been administered were used as the controls. The relations between administration time periods and tumor volumes are shown in FIGS. 9 to 11.

From these results, it was found that inhibitory effects on tumor growth was synergistically enhanced by combining taxol with CRM197.

Industrial Applicability

The present invention can be utilized for the production of the antineoplastic agent effective for the treatment of various cancers including ovarian cancers, breast cancers, prostate cancers, cancers of the uterine cervix, cancers of the uterine body, thyroid cancers, lung cancers, pancreatic cancers, stomach cancers, cancers of the colon and rectum and glioblastoma.

SEQUENCE LISTING

```
<160> NUMBER OF SEQ ID NOS: 6

<210> SEQ ID NO 1
<211> LENGTH: 560
<212> TYPE: PRT
<213> ORGANISM: Corynebacterium diphtheriae
<220> FEATURE:
<221> NAME/KEY: MOD_RES
```

<222> LOCATION: (1)
<223> OTHER INFORMATION: N-formyl-methionine

<400> SEQUENCE: 1

```
Met Ser Arg Lys Leu Phe Ala Ser Ile Leu Ile Gly Ala Leu Leu Gly
 1               5                  10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400
```

```
Asn Arg Pro Ala Tyr Ser Pro Gly His Lys Thr Gln Pro Phe Leu His
            405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
            435                 440                 445

Asn Thr Pro Leu Pro Ile Ala Gly Val Leu Leu Pro Thr Ile Pro Gly
450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
            485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
            515                 520                 525

Ile Ser Ser Asp Ser Ile Gly Val Leu Gly Tyr Gln Lys Thr Val Asp
            530                 535                 540

His Thr Lys Val Asn Ser Lys Leu Ser Leu Phe Phe Glu Ile Lys Ser
545                 550                 555                 560

<210> SEQ ID NO 2
<211> LENGTH: 1683
<212> TYPE: DNA
<213> ORGANISM: Corynebacterium diphtheriae
<220> FEATURE:
<221> NAME

| | | |
|---|---|---|
| ctc agc ctt ccc ttc gct gag ggg agt tct agc gtt gaa tat att aat<br>Leu Ser Leu Pro Phe Ala Glu Gly Ser Ser Ser Val Glu Tyr Ile Asn<br>165 170 175 | | 528 |
| aac tgg gaa cag gcg aaa gcg tta agc gta gaa ctt gag att aat ttt<br>Asn Trp Glu Gln Ala Lys Ala Leu Ser Val Glu Leu Glu Ile Asn Phe<br>180 185 190 | | 576 |
| gaa acc cgt gga aaa cgt ggc caa gat gcg atg tat gag tat atg gct<br>Glu Thr Arg Gly Lys Arg Gly Gln Asp Ala Met Tyr Glu Tyr Met Ala<br>195 200 205 | | 624 |
| caa gcc tgt gca gga aat cgt gtc agg cga tca gta ggt agc tca ttg<br>Gln Ala Cys Ala Gly Asn Arg Val Arg Arg Ser Val Gly Ser Ser Leu<br>210 215 220 | | 672 |
| tca tgc ata aat ctt gat tgg gat gtc ata agg gat aaa act aag aca<br>Ser Cys Ile Asn Leu Asp Trp Asp Val Ile Arg Asp Lys Thr Lys Thr<br>225 230 235 240 | | 720 |
| aag ata gag tct ttg aaa gag cat ggc cct atc aaa aat aaa atg agc<br>Lys Ile Glu Ser Leu Lys Glu His Gly Pro Ile Lys Asn Lys Met Ser<br>245 250 255 | | 768 |
| gaa agt ccc aat aaa aca gta tct gag gaa aaa gct aaa caa tac cta<br>Glu Ser Pro Asn Lys Thr Val Ser Glu Glu Lys Ala Lys Gln Tyr Leu<br>260 265 270 | | 816 |
| gaa gaa ttt cat caa acg gca tta gag cat cct gaa ttg tca gaa ctt<br>Glu Glu Phe His Gln Thr Ala Leu Glu His Pro Glu Leu Ser Glu Leu<br>275 280 285 | | 864 |
| aaa acc gtt act ggg acc aat cct gta ttc gct ggg gct aac tat gcg<br>Lys Thr Val Thr Gly Thr Asn Pro Val Phe Ala Gly Ala Asn Tyr Ala<br>290 295 300 | | 912 |
| gcg tgg gca gta aac gtt gcg caa gtt atc gat agc gaa aca gct gat<br>Ala Trp Ala Val Asn Val Ala Gln Val Ile Asp Ser Glu Thr Ala Asp<br>305 310 315 320 | | 960 |
| aat ttg gaa aag aca act gct gct ctt tcg ata ctt cct ggt atc ggt<br>Asn Leu Glu Lys Thr Thr Ala Ala Leu Ser Ile Leu Pro Gly Ile Gly<br>325 330 335 | | 1008 |
| agc gta atg ggc att gca gac ggt gcc gtt cac cac aat aca gaa gag<br>Ser Val Met Gly Ile Ala Asp Gly Ala Val His His Asn Thr Glu Glu<br>340 345 350 | | 1056 |
| ata gtg gca caa tca ata gct tta tcg tct tta atg gtt gct caa gct<br>Ile Val Ala Gln Ser Ile Ala Leu Ser Ser Leu Met Val Ala Gln Ala<br>355 360 365 | | 1104 |
| att cca ttg gta gga gag cta gtt gat att ggt ttc gct gca tat aat<br>Ile Pro Leu Val Gly Glu Leu Val Asp Ile Gly Phe Ala Ala Tyr Asn<br>370 375 380 | | 1152 |
| ttt gta gag agt att atc aat tta ttt caa gta gtt cat aat tcg tat<br>Phe Val Glu Ser Ile Ile Asn Leu Phe Gln Val Val His Asn Ser Tyr<br>385 390 395 400 | | 1200 |
| aat cgt ccc gcg tat tct ccg ggg cat aaa acg caa cca ttt ctt cat<br>Asn Arg Pro Ala Tyr Ser Pro Gly His Lys Thr Gln Pro Phe Leu His<br>405 410 415 | | 1248 |
| gac ggg tat gct gtc agt tgg aac act gtt gaa gat tcg ata atc cga<br>Asp Gly Tyr Ala Val Ser Trp Asn Thr Val Glu Asp Ser Ile Ile Arg<br>420 425 430 | | 1296 |
| act ggt ttt caa ggg gag agt ggg cac gac ata aaa att act gct gaa<br>Thr Gly Phe Gln Gly Glu Ser Gly His Asp Ile Lys Ile Thr Ala Glu<br>435 440 445 | | 1344 |
| aat acc ccg ctt cca atc gcg ggt gtc cta cta ccg act att cct gga<br>Asn Thr Pro Leu Pro Ile Ala Gly Val Leu Leu Pro Thr Ile Pro Gly<br>450 455 460 | | 1392 |
| aag ctg gac gtt aat aag tcc aag act cat att tcc gta aat ggt cgg<br>Lys Leu Asp Val Asn Lys Ser Lys Thr His Ile Ser Val Asn Gly Arg<br>465 470 475 480 | | 1440 |

-continued

```
aaa ata agg atg cgt tgc aga gct ata gac ggt gat gta act ttt tgt    1488
Lys Ile Arg Met Arg Cys Arg Ala Ile Asp Gly Asp Val Thr Phe Cys
            485                 490                 495 cgc cct aaa tct cct gtt tat gtt ggt aat ggt gtg cat gcg aat ctt    1536
Arg Pro Lys Ser Pro Val Tyr Val Gly Asn Gly Val His Ala Asn Leu
        500                 505                 510 cac gtg gca ttt cac aga agc agc tcg gag aaa att cat tct aat gaa    1584
His Val Ala Phe His Arg Ser Ser Ser Glu Lys Ile His Ser Asn Glu
    515                 520                 525 att tcg tcg gat tcc ata ggc gtt ctt ggg tac cag aaa aca gta gat    1632
Ile Ser Ser Asp Ser Ile Gly Val Leu Gly Tyr Gln Lys Thr Val Asp
530                 535                 540 cac acc aag gtt aat tct aag cta tcg cta ttt ttt gaa atc aaa agc    1680
His Thr Lys Val Asn Ser Lys Leu Ser Leu Phe Phe Glu Ile Lys Ser
545                 550                 555                 560 tga                                                                 1683
```

<210> SEQ ID NO 3
<211> LENGTH: 560
<212> TYPE: PRT
<213> ORGANISM: Corynebacterium diphtheriae

<400> SEQUENCE: 3

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile G

```
                260                 265                 270
Glu Glu Phe His Gln Thr Ala Leu Glu His Pro Glu Leu Ser Glu Leu
                275                 280                 285
Lys Thr Val Thr Gly Thr Asn Pro Val Phe Ala Gly Ala Asn Tyr Ala
                290                 295                 300
Ala Trp Ala Val Asn Val Ala Gln Val Ile Asp Ser Glu Thr Ala Asp
305                 310                 315                 320
Asn Leu Glu Lys Thr Thr Ala Ala Leu Ser Ile Leu Pro Gly Ile Gly
                325                 330                 335
Ser Val Met Gly Ile Ala Asp Gly Ala Val His His Asn Thr Glu Glu
                340                 345                 350
Ile Val Ala Gln Ser Ile Ala Leu Ser Ser Leu Met Val Ala Gln Ala
                355                 360                 365
Ile Pro Leu Val Gly Glu Leu Val Asp Ile Gly Phe Ala Ala Tyr Asn
                370                 375                 380
Phe Val Glu Ser Ile Ile Asn Leu Phe Gln Val Val His Asn Ser Tyr
385                 390                 395                 400
Asn Arg Pro Ala Tyr Ser Pro Gly His Lys Thr Gln Pro Phe Leu His
                405                 410                 415
Asp Gly Tyr Ala Val Ser Trp Asn Thr Val Glu Asp Ser Ile Ile Arg
                420                 425                 430
Thr Gly Phe Gln Gly Glu Ser Gly His Asp Ile Lys Ile Thr Ala Glu
                435                 440                 445
Asn Thr Pro Leu Pro Ile Ala Gly Val Leu Leu Pro Thr Ile Pro Gly
                450                 455                 460
Lys Leu Asp Val Asn Lys Ser Lys Thr His Ile Ser Val Asn Gly Arg
465                 470                 475                 480
Lys Ile Arg Met Arg Cys Arg Ala Ile Asp Gly Asp Val Thr Phe Cys
                485                 490                 495
Arg Pro Lys Ser Pro Val Tyr Val Gly Asn Gly Val His Ala Asn Leu
                500                 505                 510
His Val Ala Phe His Arg Ser Ser Glu Lys Ile His Ser Asn Glu
                515                 520                 525
Ile Ser Ser Asp Ser Ile Gly Val Leu Gly Tyr Gln Lys Thr Val Asp
                530                 535                 540
His Thr Lys Val Asn Ser Lys Leu Ser Leu Phe Phe Glu Ile Lys Ser
545                 550                 555                 560
```

<210> SEQ ID NO 4
<211> LENGTH: 1683
<212> TYPE: DNA
<213> ORGANISM: Corynebacterium diphtheriae

<400> SEQUENCE: 4

```
gtgagcagaa aactgtttgc gtcaatctta at

-continued

```
ctcagccttc ccttcgctga ggggagttct agcgttgaat atattaataa ctgggaacag    540
gcgaaagcgt taagcgtaga acttgagatt aattttgaaa cccgtggaaa acgtggccaa    600
gatgcgatgt atgagtatat ggctcaagcc tgtgcaggaa atcgtgtcag gcgatcagta    660
ggtagctcat tgtcatgcat aaatcttgat tgggatgtca taaggataaa actaagaca    720
aagatagagt ctttgaaaga gcatggccct atcaaaaata aaatgagcga aagtcccaat    780
aaaacagtat ctgaggaaaa agctaaacaa tacctagaag aatttcatca aacggcatta    840
gagcatcctg aattgtcaga acttaaaacc gttactggga ccaatcctgt attcgctggg    900
gctaactatg cggcgtgggc agtaaacgtt gcgcaagtta tcgatagcga aacagctgat    960
aatttggaaa agacaactgc tgctctttcg atacttcctg gtatcggtag cgtaatgggc   1020
attgcagacg gtgccgttca ccacaataca gaagagatat ggcacaatc aatagcttta   1080
tcgtctttaa tggttgctca agctattcca ttggtaggag agctagttga tattggtttc   1140
gctgcatata attttgtaga gagtattatc aatttatttc aagtagttca taattcgtat   1200
aatcgtcccg cgtattctcc ggggcataaa acgcaaccat ttcttcatga cgggtatgct   1260
gtcagttgga acactgttga agattcgata atccgaactg gttttcaagg ggagagtggg   1320
cacgacataa aaattactgc tgaaaatacc ccgcttccaa tcgcgggtgt cctactaccg   1380
actattcctg gaaagctgga cgttaataag tccaagactc atatttccgt aaatggtcgg   1440
aaaataagga tgcgttgcag agctatagac ggtgatgtaa cttttttgtcg ccctaaatct   1500
cctgtttatg ttggtaatgg tgtgcatgcg aatcttcacg tggcatttca cagaagcagc   1560
tcggagaaaa ttcattctaa tgaaatttcg tcggattcca taggcgttct tgggtaccag   1620
aaaacagtag atcacaccaa ggttaattct aagctatcgc tattttttga aatcaaaagc   1680
tga                                                                1683
```

<210> SEQ ID NO 5
<211> LENGTH: 385
<212> TYPE: PRT
<213> ORGANISM: Corynebacterium diphtheriae

<400> SEQUENCE: 5

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg As

```
Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Ile Glu Gly
            210                 215                 220

Arg Gly Ile Pro Ala Tyr Ser Pro Gly His Lys Thr Gln Pro Phe Leu
225                 230                 235                 240

His Asp Gly Tyr Ala Val Ser Trp Asn Thr Val Glu Asp Ser Ile Ile
            245                 250                 255

Arg Thr Gly Phe Gln Gly Glu Ser Gly His Asp Ile Lys Ile Thr Ala
            260                 265                 270

Glu Asn Thr Pro Leu Pro Ile Ala Gly Val Leu Leu Pro Thr Ile Pro
            275                 280                 285

Gly Lys Leu Asp Val Asn Lys Ser Lys Thr His Ile Ser Val Asn Gly
            290                 295                 300

Arg Lys Ile Arg Met Arg Cys Arg Ala Ile Asp Gly Asp Val Thr Phe
305                 310                 315                 320

Cys Arg Pro Lys Ser Pro Val Tyr Val Gly Asn Gly Val His Ala Asn
            325                 330                 335

Leu His Val Ala Phe His Arg Ser Ser Glu Lys Ile His Ser Asn
            340                 345                 350

Glu Ile Ser Ser Asp Ser Ile Gly Val Leu Gly Tyr Gln Lys Thr Val
            355                 360                 365

Asp His Thr Lys Val Asn Ser Lys Leu Ser Leu Phe Phe Glu Ile Lys
            370                 375                 380

Ser
385

<210> SEQ ID NO 6
<211> LENGTH: 1158
<212> TYPE: DNA
<213> ORGANISM: Corynebacterium diphtheriae
<220> FEATURE

| | | |
|---|---|---|
| gga gcg gtt ttg gat att aga tac ggt gtt tcg aga att gca tat agt<br>Gly Ala Val Leu Asp Ile Arg Tyr Gly Val Ser Arg Ile Ala Tyr Ser<br>100 105 110 | | 336 |
| aaa gac ttt gaa act ctc aaa gtt gat ttt ctt agc aag cta cct gaa<br>Lys Asp Phe Glu Thr Leu Lys Val Asp Phe Leu Ser Lys Leu Pro Glu<br>115 120 125 | | 384 |
| atg ctg aaa atg ttc gaa gat cgt tta tgt cat aaa aca tat tta aat<br>Met Leu Lys Met Phe Glu Asp Arg Leu Cys His Lys Thr Tyr Leu Asn<br>130 135 140 | | 432 |
| ggt gat cat gta acc cat cct gac ttc atg ttg tat gac gct ctt gat<br>Gly Asp His Val Thr His Pro Asp Phe Met Leu Tyr Asp Ala Leu Asp<br>145 150 155 160 | | 480 |
| gtt gtt tta tac atg gac cca atg tgc ctg gat gcg ttc cca aaa tta<br>Val Val Leu Tyr Met Asp Pro Met Cys Leu Asp Ala Phe Pro Lys Leu<br>165 170 175 | | 528 |
| gtt tgt ttt aaa aaa cgt att gaa gct atc cca caa att gat aag tac<br>Val Cys Phe Lys Lys Arg Ile Glu Ala Ile Pro Gln Ile Asp Lys Tyr<br>180 185 190 | | 576 |
| ttg aaa tcc agc aag tat ata gca tgg cct ttg cag ggc tgg caa gcc<br>Leu Lys Ser Ser Lys Tyr Ile Ala Trp Pro Leu Gln Gly Trp Gln Ala<br>195 200 205 | | 624 |
| acg ttt ggt ggt ggc gac cat cct cca aaa tcg gat ctg atc gaa ggt<br>Thr Phe Gly Gly Gly Asp His Pro Pro Lys Ser Asp Leu Ile Glu Gly<br>210 215 220 | | 672 |
| cgt ggg atc ccc gcg tat tct ccg ggg cat aaa acg caa cca ttt ctt<br>Arg Gly Ile Pro Ala Tyr Ser Pro Gly His Lys Thr Gln Pro Phe Leu<br>225 230 235 240 | | 720 |
| cat gac ggg tat gct gtc agt tgg aac act gtt gaa gat tcg ata atc<br>His Asp Gly Tyr Ala Val Ser Trp Asn Thr Val Glu Asp Ser Ile Ile<br>245 250 255 | | 768 |
| cga act ggt ttt caa ggg gag agt ggg cac gac ata aaa att act gct<br>Arg Thr Gly Phe Gln Gly Glu Ser Gly His Asp Ile Lys Ile Thr Ala<br>260 265 270 | | 816 |
| gaa aat acc ccg ctt cca atc gcg ggt gtc cta cta ccg act att cct<br>Glu Asn Thr Pro Leu Pro Ile Ala Gly Val Leu Leu Pro Thr Ile Pro<br>275 280 285 | | 864 |
| gga aag ctg gac gtt aat aag tcc aag act cat att tcc gta aat ggt<br>Gly Lys Leu Asp Val Asn Lys Ser Lys Thr His Ile Ser Val Asn Gly<br>290 295 300 | | 912 |
| cgg aaa ata agg atg cgt tgc aga gct ata gac ggt gat gta act ttt<br>Arg Lys Ile Arg Met Arg Cys Arg Ala Ile Asp Gly Asp Val Thr Phe<br>305 310 315 320 | | 960 |
| tgt cgc cct aaa tct cct gtt tat gtt ggt aat ggt gtg cat gcg aat<br>Cys Arg Pro Lys Ser Pro Val Tyr Val Gly Asn Gly Val His Ala Asn<br>325 330 335 | | 1008 |
| ctt cac gtg gca ttt cac aga agc agc tcg gag aaa att cat tct aat<br>Leu His Val Ala Phe His Arg Ser Ser Ser Glu Lys Ile His Ser Asn<br>340 345 350 | | 1056 |
| gaa att tcg tcg gat tcc ata ggc gtt ctt ggg tac cag aaa aca gta<br>Glu Ile Ser Ser Asp Ser Ile Gly Val Leu Gly Tyr Gln Lys Thr Val<br>355 360 365 | | 1104 |
| gat cac acc aag gtt aat tct aag cta tcg cta ttt ttt gaa atc aaa<br>Asp His Thr Lys Val Asn Ser Lys Leu Ser Leu Phe Phe Glu Ile Lys<br>370 375 380 | | 1152 |
| agc tga<br>Ser<br>385 | | 1158 |

The invention claimed is:

1. An antineoplastic agent formulated for treating breast cancer characterized by combining (a) at least one of paclitaxel or irinotecan with (b) a protein which is a diphtheria toxin mutant having an activity to inhibit a binding between HB-EGF and EGFR and substantially not having toxicity of diphtheria toxin, wherein the paclitaxel is used in an amount equivalent a 0.875 to 1.375 mg dose per kilogram body weight, and the irinotecan is used in an amount equivalent to a 0.5 to 0.75 mg dose per kilogram body weight.

2. The antineoplastic agent formulated for treating breast cancer according to claim 1, wherein said protein comprises at least a receptor-binding domain with no mutation in an amino acid sequence of diphtheria toxin.

3. The antineoplastic agent formulated for treating breast cancer according to claim 1, wherein said protein is a protein composed of an amino acid sequence having one or more amino acid deletions, substitutions or additions in the amino acid sequence of diphtheria toxin.

4. The antineoplastic agent formulated for treating breast cancer according to claim 1, wherein said protein is either CRM197 or DT52E148K.

5. A method for treating breast cancer comprising administering (a) at least one of paclitaxel or irinotecan in combination with (b) a protein which is a diphtheria toxin mutant having an activity to inhibit a binding between HB-EGF and EGFR and substantially not having toxicity of diphtheria toxin wherein (a) and (b) are administered in amounts in which both independently have no sufficient anticancer action but the anticancer action is elicited by combining both (a) and (b).

6. A kit for treating breast cancer composed of (a) at least one of paclitaxel or irinotecan and (b) the protein which is diphtheria toxin mutant having the activity to inhibit the binding between HB-EGF and EGFR and substantially not having the toxicity of diphtheria toxin in amounts in which both independently have no sufficient anticancer action but the anticancer action is elicited by combining both (a) and (b).

7. An antineoplastic agent composition formulated for treating breast cancer composed of (a) at least one of paclitaxel or irinotecan and (b) a protein which is a diphtheria toxin mutant having an activity to inhibit a binding between HB-EGF and EGFR and substantially not having toxicity of diphtheria toxin in amounts in which both independently have no sufficient anticancer action but the anticancer is elicited by combining both (a) and (b).

8. The antineoplastic agent formulated for treating breast cancer according to claim 1, wherein (a) is paclitaxel.

9. The antineoplastic agent formulated for treating breast cancer according to claim 1, wherein (a) is irinotecan.

10. The antineoplastic agent formulated for teating breast cancer according to claim 1, wherein said protein comprises CRM197.

* * * * *